US007179491B1

(12) United States Patent
Mag

(10) Patent No.: US 7,179,491 B1
(45) Date of Patent: Feb. 20, 2007

(54) PROCESS OF CONVERTING RENDERED TRIGLYCERIDE OIL FROM MARINE SOURCES INTO BLAND, STABLE OIL

(76) Inventor: Ted Mag, 35 Old Church Road, King City, Ontario (CA) L7B 1K4

( * ) Notice: Subject to any disclaimer, the term of this patent is extended or adjusted under 35 U.S.C. 154(b) by 0 days.

(21) Appl. No.: 09/890,383

(22) PCT Filed: Jan. 28, 2000

(86) PCT No.: PCT/CA00/00078

§ 371 (c)(1),
(2), (4) Date: Jan. 22, 2002

(87) PCT Pub. No.: WO00/44862

PCT Pub. Date: Aug. 3, 2000

(30) Foreign Application Priority Data

Jan. 29, 1999 (CA) ................................. 2260397

(51) Int. Cl.
A61K 35/34 (2006.01)
A61K 35/60 (2006.01)

(52) U.S. Cl. ...................... 424/522; 424/523; 424/524

(58) Field of Classification Search ............... 424/522, 424/523, 524
See application file for complete search history.

(56) References Cited

U.S. PATENT DOCUMENTS

| 4,093,540 A | * | 6/1978 | Sen Gupta .................... 554/80 |
| 4,623,488 A | | 11/1986 | Takao ........................ 554/224 |
| 4,629,588 A | | 12/1986 | Welsh et al. |
| 4,678,808 A | * | 7/1987 | Ward et al. ................. 514/560 |
| 4,734,226 A | | 3/1988 | Parker et al. |
| 4,780,309 A | * | 10/1988 | Geria et al. .................... 424/45 |
| 4,787,981 A | | 11/1988 | Tanahashi et al. |
| 4,874,629 A | | 10/1989 | Chang et al. ............... 426/601 |
| 4,880,574 A | | 11/1989 | Welsh ........................ 554/176 |
| 4,956,126 A | | 9/1990 | Staal et al. |
| 5,053,169 A | | 10/1991 | Price |
| 5,069,829 A | | 12/1991 | Van Dalen et al. ......... 554/191 |
| 5,079,208 A | | 1/1992 | Lammers et al. |
| 5,130,061 A | | 7/1992 | Cornieri et al. |
| 5,149,851 A | | 9/1992 | Stout et al. |
| 5,264,597 A | | 11/1993 | Van Dalen et al. ......... 554/191 |
| 5,336,794 A | * | 8/1994 | Pryor et al. ................. 554/206 |
| 5,415,879 A | | 5/1995 | Oh |
| 5,693,835 A | | 12/1997 | Konishi et al. |
| 5,720,980 A | | 2/1998 | Cohen |
| 5,840,945 A | | 11/1998 | Tsujiwaki et al. |
| 5,855,944 A | | 1/1999 | Koschinski et al. ........ 426/541 |

FOREIGN PATENT DOCUMENTS

| CA | 2260397 | 7/2000 |
| DE | 36 43 848 A | 9/1988 |
| EP | 292846 | 11/1986 |
| JP | 59176264 A | 10/1984 |
| JP | 62093234 A | 4/1987 |
| JP | 6116585 A | 4/1994 |
| WO | 9628150 | * 9/1996 |
| WO | WO 96/28150 | 9/1996 |

OTHER PUBLICATIONS

Wanasundara et al., Journal of Food Lipids 5(1): 29-41 (1998).*
V. K. S. Shuklia, et al., *Rancidity in Encapsulated Heath-food Oils*, INFORM, Oct. 1998, vol. 9, No. 10.
L. Businco, et al., *Breast Milk from Mothers of Children with Newly Developed Atopic Eczema Has Low Levels of Long Chain Polyunsaturated Fatty Acids*, Journal Allergy Clinical Immunology, Jun. 1993, at 91(6):1134-9.
M. Leichsenring, et al., *Polyunsaturated Fatty Acids in Erythrocyte and Plasma Lipids of Children with Severe Protein-Energy Malnutrition*, ACTA Paediatr, May 1995, at 84(5):516-20.
R. A. Henderson, et al., *Effect of Fish Oil on the Fatty Acid Composition of Human Milk and Maternal and Infant Erythrocytes*, LIPIDS, Nov. 1992, at 27(11):863-69.
M.A. Crawford, et al., *Essential Fatty Acids and Fetal Brain Growth*, LANCET, Feb. 28, 1976, at I(7957):452-53.
G. Yu, et al., *Polyunsaturated Fatty Acids in School Children in Relation to Allergy and Serum IgE Levels*, Pediatric Allergy Immunology, Aug. 1998, at 9(3):133-38.

(Continued)

Primary Examiner—Jean C. Witz
(74) Attorney, Agent, or Firm—Synnestvedt & Lechner LLP

(57) ABSTRACT

Triglyceride oil derived from marine sources, mammalian and fish, is treated with a silica at relatively low temperature under vacuum and is then further treated with a bleaching clay under vacuum and at higher temperature. The silica and the bleaching clay are then separated from the oil. The oil treated by this method is essentially free of proteinaceous materials, phosphatides and mucilage, pro-oxidant metals and very low in colored compounds, and is suitable for deodorizing. The deodorized oil is completely bland, unchanged in the concentration of the long-chain highly unsaturated fatty acids (EPA, DPA and DHA), very low in color, peroxides and secondary oxidation products, free of pesticides and has very good flavor stability. The method avoids the use of any chemicals, such as in the acid and base treatments required in conventional degumming and alkali refining of oils of marine origin. This avoids the formation of artifacts in the oil and trace contamination with chemicals. It also reduces the number of process steps required to produce deodorized food oil from marine sources, which is advantageous in respect to oil quality, process losses and processing costs. The method is especially environmentally advantageous, since it avoids the need for soapstock and waste water processing entirely. Refined oil produced by the method is useful as a nutritional supplement and in methods of therapy or medical treatment.

24 Claims, No Drawings

OTHER PUBLICATIONS

G. Yu, et al., *Serum Levels of Phospholipids Fatty Acids in Mothers and Their Babies in Relation to Allergic Disease*, European Journal of Pediatrics, Apr. 1998, at 157(4):298-303.

C. Benistant, et al., *Docosapentaenoic acid (22:5,n-3): Metabolism and Effect on Prostacyclin Production in Endothelial Cells*, Prostaglandins Leukot Essesnt Fatty Acids, Oct. 1996, at 55(4):287-92.

V. K. S. Shukla, et al., *The Presence of Oxidative Polymeric Materials in Encapsulated Fish Oils*, LIPIDS, 1991, at 26:23-26.

K. L. Fritshe, et al., *Rapid Autoxidation of Fish Oil in Diets Without Added Antioxidants*, Journal of Nutrition, 1998, at 118:425-426.

D. Harats, et al., *Fish Oil Ingestion in Smokers and Nonsmokers Enhances Peroxidation of Plasma Lipoproteins*, Atherosclerosis, 1991, at 90:127-139.

N. Kromann, et al., *Epidemiological Studies in the Upernavik District, Greenland*, 208 Acta Med Scand, 1980, at 208:401-06.

D. Kromhout, et al., *Inverse Relation Between Fish Oil Consumption and 20 Year Mortality From Coronary Heart Disease*, New England Journal of Medicine, 312:1205-09 (1985).

K. N. Seidelin, et al., *N-3 Fatty Acids in Adipose Tissue and Coronary Artery Disease Are Inversely Related*, American Journal of Clinical Nutrition, 55:1117-19 (1992).

D. Ornish, et al., *Can Lifestyle Changes Reverse Coronary Heart Disease*, LANCET, 336:129-33 (1990).

J. F. Belch, et al., *Effects of Altering Dietary Essential Fatty Acids on Requirements for Non-steroidal Anti-inflammatory Drugs in Patients with Rheumatoid Arthritis: A Double Blind Placebo Controlled Study*, Annals of Rheumatoidal Disorders, 47:96-104 (1988).

M. G. Murphy, et al., *Diets Enriched in Menhaden Fish Oil, Seal Oil, or Shark Liver Oil Have Distinct Effects on the Lipid and Fatty-acid Composition of Guinea Pig Heart*, Molecular Cell Biochemistry, 177(1-2):257-69 (Dec. 1997).

T. Kanayasu-Toyoda, et al., *Docosapentaenoic Acid (22:5,n-3), an Elongation Metabolite of Eicosapentaenoic Acid (20:5, n-3), Is a Potent Simulator of Endothelial Cell Migration on Pretreatment In Vitro*, Prostaglandis Leukot Essent Fatty Acids, 54(5):319-25 (May 1996).

U. N. Wanasundara, et al., *Antioxidant and Pro-oxidant Activity of Green Tea Extracts in Marine Oils*, Food Chemistry, 63(3):335-42 (1998).

E. Vognid, et al., *Effects of Dietary Marine Oils and Olive Oil on Fatty Acid Compositon, Platelet Membrane Fluidity, Platelet Responses, and Serum Lipids in Healthy Humans*, LIPIDS, 33(4):427-36 (1998).

F. Shahidi. "Seat Fishery and Product Development." ScienceTech Publishing Company, St. John's, Canada, pp. 109-111, 1998.

"Edible Oil Processing," In Y.H. Hui (ed.), *Bailey's Industrial Oil and Fat Products*, 5th ed., vol. 2, Edible Oil and Fat Products: Oils and Oilseeds, John Wiley & Sons, Inc., pp. 517-540, 1995.

"Storing and Processing of Cottonseed and Refining Cottonseed Oil," In Y.H. Hui (ed.), *Bailey's Industrial Oil and Fat Products*, 5th ed., vol. 2, Edible Oil and Fat Products: Oils and Oilseeds, John Wiley & Sons, Inc., pp. 176-181, 1995.

Engelhard Corporation. Grade F-105. Last Update Aug. 1998.

Crosfield. Sorbsil R. Issue No. 1, Apr. 1984.

\* cited by examiner

PROCESS OF CONVERTING RENDERED TRIGLYCERIDE OIL FROM MARINE SOURCES INTO BLAND, STABLE OIL

This application is a U.S. national stage application based on International Application No. PCT/CA00/00078, filed Jan. 28, 2000, which claims the benefit of the filing date of Canadian Application No. 2,260,397, filed Jan. 29, 1999

FIELD OF THE INVENTION

The invention relates to a commercial scale method of preparing a bland and flavor stable triglyceride food oil rendered from the tissue fat of fish and marine mammals without the use of refining chemicals such as alkali or acid.

BACKGROUND OF THE INVENTION (i) Omega-3 Essential Fatty Acids

Health experts have concluded that a large percentage of the population have a diet which is deficient in long chain, highly unsaturated essential fatty acids. For example, it is estimated that 80% of all Americans have a deficiency. As many as 60 medical conditions are linked to this deficiency or have been identified as benefiting from Omega-3 supplementation.

The three most important of the long chain fatty acids are eicosapentaenoic acid (EPA), docosahexaenoic acid (DHA), and docosapentaenoic (DPA). These fatty acids are deemed "essential" because they have a vital role in maintaining the integrity and fluidity of the membrane which surrounds human cells and because they cannot be synthesized by the body. Without a healthy membrane, the ability of cells to hold water, nutrients and electrolytes is impaired. As a consequence, the membrane may no longer protect the cell from damage caused by free radicals which are the products of oxidation within the body. They also lose their receptivity to hormones and their ability to relay chemically encoded instructions for cellular repair.

The search by health conscious consumers for foods containing omega-3 fatty acids can be a frustrating one. Given the trend toward mass production and packaging of meals and meal ingredients, consumers have less knowledge of, or influence over the contents of their food. The move by some manufacturers toward mono or polyunsaturated fats as substitutes for saturated fats is a positive step. Generally however, the polyunsaturates most often selected are those derived from vegetable oils which contain significant amounts of omega 6 but little or no omega-3. While omega 6 and omega-3 fatty acids are both necessary to good health, most health experts agree that, they should be consumed in a balance of 4:1 respectively. Today's Western diet has created a serious imbalance with current consumption on average of 20 times more omega 6 than omega-3. Concerned consumers have begun to look for health food supplements to restore the equilibrium. Three major sources of omega-3 supplements are flaxseed oil, fish oils, and seal oil.

The past decade has seen rapid growth in the production of flaxseed and fish oils. Both types of oil are considered to be good dietary sources of polyunsaturated fats but are less effective than seal oil in supplying omega-3 fatty acids. Flaxseed oil contains no EPA, DHA or DPA but rather contains alpha-linolenic acid—a precursor to EPA. There is evidence however that the rate of metabolic conversion can be slow and unreliable. Some research has shown that supplementation with flaxseed oil may result in higher tissue levels of alpha-linolenic acid without any corresponding increase in EPA.

Fish oils vary considerably in the type and level of fatty acid composition depending on the particular species and their diets. For example, fish raised by aquaculture tend to have a lower level of omega-3 fatty acids than those in the wild. some research has shown that seal oil is more beneficial to those at risk of heart disease and diabetes than is fish oil. The relative absence of DPA in fish oil and the slower rate at which the body assimilates EPA and DHA from fish oils have been cited as factors.

The most direct and complete source of omega-3 oils is found in the blubber of certain marine mammals, especially the harp seal. Among its advantages is that the body's absorption of omega-3 from seal blubber is faster and more thorough than is the case with flaxseed and fish oils. This is due, in part, to the molecular configurations of the EPA and DHA in seal oil which varies slightly from that found in fish oils. The essential fatty acids found in seal oil include a high level of DPA (up to ten times that of fish oils). There is growing evidence that DPA is the most important of the essential fatty acids in keeping artery walls soft and plaque free. A further advantage of seal oil is that it is more stable than fish oil and less vulnerable to the natural process of oxidation. However, there are challenges in producing a satisfactory grade seal oil for administration as a dietary supplement to humans. Seal oils, like other health food oils, are susceptible the natural process of oxidation. The primary and secondary products of oxidation may give rise to unacceptable flavours and odours in the oil, impair digestibility of the oil, and produce fee radicals which can damage or destroy the body's cells.

The causes of oxidation include exposure to air, heat, light ("harmful light" refers to light in the range of about 4,250–5,100 angstrom), oxygen and certain metals such as iron. Oxidation of polyunsaturated oils limit their shelf life. As fish and seal oils become oxidized their taste and odour may become objectionalble. For example, one study of encapsulated fish and plant oil samples found that many commercially prepared oils had poor oxidative stability (VKS Shuklia, EG Perkins, "Rancidity in encapsulated health-food oils", Inform, vol. 9, no. 10 (October 1998)). Clearly there is a need for nutritional oils that offer higher levels of oxidative stability.

Health Canada recommends that the daily diet contain at least 1.8 grams of omega-3 fatty acids. The U.S. Department of Health and Nutrition Services has also acknowledged that health benefits would accrue to the general population if dietary intakes of omega-3 polyunsaturated fatty acids (PUFA) were increased. At present, the average consumption of omega-3 PUFA in North America and Europe is less than one gram per day. The administration of seal oil as a dietary supplement could fill this gap if a suitable refined oil could be produced.

(ii) Oil Refining

In the processing of food oils and fats from animal, vegetable and marine sources, it is important to produce edible oil and fat products that have a bland, neutral taste for several months after processing. To obtain an oil with these characteristics, it is essential to remove compounds that give flavor to the oil as well as compounds that are detrimental to oxidative stability. It is also desirable to significantly reduce, if not eliminate, chemical contaminants such as PCBs and pesticides.

The concentrations of objectionable compounds vary in the different oils, depending on the source. Many of the common vegetable oils contain phosphatides, colored compounds and their breakdown products, oxidation products of triglycerides, dissolved and suspended proteinaceous material, free fatty acids, pesticides, pro-oxidant metals and pesticides.

Oils derived from marine sources, mammalian and fish, are very low in phosphatides and may be low in colored compounds, but proteinaceous and mucilagenous materials, breakdown products from triglyceride oxidation, and concentrations of calcium and magnesium and pro-oxidant metals are more significant, as well as pesticides. Most importantly, these oils are more sensitive to oxidative deterioration because of the highly unsaturated fatty acids present. They also contain only insignificant amounts of natural antioxidants, such as the tocopherols that are present in significant amounts in most vegetable oils.

The oils of marine origin also have a very intense fishy odor and taste, which originates with protein, mucilage and triglyceride breakdown products. The odor and taste compounds and their precursors must be removed to extremely low levels to make the oil more suitable for food uses and to improve their flavor stability after processing.

Experience in processing the oils from the above sources has shown that to achieve sufficiently complete removal of objectionable substances requires several 'refining' steps. These refining steps are described for the various oils in Bailey's Industrial Oil & Fat Products, Fifth Edition, Volume 2. The refining steps comprise the following:

Degumming—alkali refining—bleaching—deodorizing.

The degumming process serves to remove phosphatides and other mucilagenous compounds from the oil and is especially important with vegetable oils. Water alone, water and acids such as phosphoric acid, or water and other chemicals are used. Using water alone does not remove phosphatides to the required low concentration.

The alkali refining process serves to remove free fatty acids and phosphatides, especially the non-hydratable phosphatides, mucilagenous and proteinaceous material to very low concentrations. Some of the coloured compounds and the trace metals that occur in oils are also removed. Sodium hydroxide solution is commonly used, sometimes after a pretreatment with an acid such as phosphoric acid. Serious disadvantages of the process are that oil losses tend to be high (because of entrainment of oil in the soap phase), and there is a need to remove fat and chemicals from the water in the process to make it acceptable for discharge. U.S. Pat. No. 5,855,944 (Kochinski, 1999) and U.S. Pat. No. 5,264,597 (Van Dalen et al., 1993) are two examples of prior art patents that use alkali refining.

The alkali refined oil is water-washed to remove small amounts of soap and phosphatides. Water washing is sometimes replaced by treating the oil with small amounts of silica gel, which serves to remove residual amounts of phosphatides and soaps before bleaching. This saves some of the water treatment costs associated with alkali refining.

Bleaching with activated bleaching earth is used to remove colored compounds, especially chlorophylloid and carotenoid material, but also small amounts of phosphatides and soap still left in the oil after alkali refining.

Deodorization primarily removes flavor and odor compounds and small amounts of free fatty acids by distillation. The process is carried out at very low pressures and relatively high temperatures (about 260° C.) using steam as a carrier gas to strip the volatile flavor and odor compounds and free fatty acids from the oil. The success of this step depends on the oil having been thoroughly 'refined' in the processing steps outlined above, except for removal of free fatty acids. Because of the relatively high temperatures that must be used in deodorizing, inadequate removal of flavor and color precursors easily lead to new formation of such compounds and hence oils of poor flavor and flavor stability and high color.

The above sequence of processing, or 'refining' steps is sometimes modified. For example, degumming and alkali refining can be combined in a single operation followed by bleaching and deodorizing.

Further, alkali refining can be omitted in some cases in favor of degumming alone with chemicals and water. This is then followed by an acid treatment of the oil before adding bleaching clay and bleaching the oil, and then deodorizing. Alternatively, chemically degummed oil may be treated with silica gel to reduce phosphatides still further, as is described, for example in U.S. Pat. No. 5,069,829 to Van Dalen et al, and in U.S. Pat. No. 4,880,574 to Welsh.

When alkali refining is not used, the deodorizing step is relied upon to remove the free fatty acids from the original, relatively high concentration in the oil to the required low concentration, as mentioned earlier. There are, thus, no fatty acid soaps to be processed and waste water to be treated, as in alkali refining, and the process losses are lower. The deodorizing conditions, however must be somewhat more extreme than are applied with alkali refined oils (temperature, time, steam usage). It is important to note that with vegetable oils and animal fats, which do not contain highly unsaturated fatty acids, the danger of isomerization when somewhat extreme deodorizing temperatures and times are used is not a factor, but with unhydrogenated oils of marine origin this has not been done.

Oils of marine origin are invariably alkali refined and may receive an acid pretreatment before alkali refining to precipitate calcium, magnesium and other trace elements, which are then removed in the alkali refining step. The processing of oils of marine origin is described in Seal Fishery and Product Development, F. Shahidi, p. 109–111, Science Tech Publishing Company, St. John's NF, 1998. Chang in U.S. Pat. No. 4,874,629 and Takao in U.S. Pat. No. 4,623,488 refer to this along with bleaching as part of the processing steps required to produce fish oils for food use.

Because of their high unsaturation and ease of oxidation and, hence, their great sensitivity with respect to achieving a bland, flavor stable product for use in edible oil products, it is very important to achieve essentially total removal of the deleterious components in the crude oil. This is required even when these oils are hydrogenated to make them more saturated and stable towards oxidation before use as a food. The danger of inadequate removal, especially of soluble proteinaceous materials and of pro-oxidant metals, primarily iron, and of other deleterious compounds when alkali refining is not applied, is considered too great.

As discussed above, there is now emphasis on using oils of marine origin, unhydrogenated, for their special nutritional qualities due to their content of highly unsaturated, long-chain fatty acids (eicosapentaenoic acid, docosapentaenoic acid and docosahexaenoic acid, usually described as EPA, DPA and DHA, or as omega-3 fatty acids) in their triglycerides. Hydrogenation to achieve better stability would destroy the special nutritional qualities of these fatty acids. With the unhydrogenated oils, the thorough removal of oil components deleterious to achieving a bland, flavor-stable oil is then even more important than with other oils.

At the same time, it is also advantageous with these highly sensitive oils to reduce the refining steps and eliminate the use of chemicals as much as possible. This minimizes the chances for exposure to air, and the need for repeated heating of the oils, or for extended periods of time, and the chance for the formation of chemical artifacts with the highly unsaturated fatty acids present. If achieved, it would then be possible to provide an oil for nutraceutical and other food uses that has excellent organoleptic properties without any decrease in the concentration of the nutritionally important EPA, DPA and DHA, and with a minimum of breakdown products, free fatty acids, colored compounds, pro-oxidant metals, pesticide residues and chemical artifacts.

SUMMARY OF THE INVENTION

It was found that oils from marine sources, mammalian and fish, can be 'refined' to achieve essentially complete removal of compounds that are deleterious to oil quality without the use of degumming or alkali refining, or the use of any chemical compounds such as acids or bases.

The process of the invention produces polyunsaturated oils that are rich in the omega-3 fatty acids, particular EPA, DHA &, in the case of seal oil, DPA. The resulting oils have low levels of oxidation and high oxidative stability. The oils have very low levels of lipid peroxides and secondary oxidation products. The process provides a marine mammal (preferably seal) oil, or alternatively a fish oil, with its original omega-3 content unchanged and yet with oxidative characteristics superior to those derived from other methods of preparation. In addition to their oxidative stability, the oils derived from mammalian marine sources offer more efficient assimilation in the body, and include DPA as a high value fatty acid. The refined marine oil (from mammalian or fish sources), has the following properties:
  essentially bland in taste,
  essentially odorless,
  when the oil is deodorized, a free fatty acid content below about 0.25%, preferably below about 0.0% and most preferably below about 0.08% or below about 0.06%; when the oil is not deodorized, the free fatty acid content is below about <2%, preferably below about 1%, below about 0.5% and most preferably below about 0.2% (these values apply to fish oil or seal oil),
  a peroxide value below about 1.5 me/Kg, preferably about 1.0 me/kg or most preferably at about zero me/kg,
  an anisidine value below about 5 and most preferably below about 2,
  iron below about 0.1 mg/kg and most preferably below the detection limit,
  copper below about 0.05 mg/kg,
  phosphorus, below about 0.2 mg/kg,
  all pesticides considered deleterious in the food chain, below their detection limits as preferably measured chromatographically,
  a content of omega-3 fatty acids that is about unchanged from the crude oil, within analysis error, and a flavor stability by organoleptic testing in which no strong flavor development occurs for two months and preferably three months and most preferably 4 months at ambient temperatures when the oil is protected from harmful light radiation and from air, with or without the addition of antioxidants,
  no production of waste water or soapstock byproduct (i.e. it is an environmentally friendly oil).

Preferred marine sources of crude, rendered oil are, for example, the blubber from various seal species and especially harp seal, which is the most abundant in Canadian waters, and fish preferably with a high ratio of edible tissue to offal, such as salmon, mackerel, tuna, bluefish, sardines, anchovies, halibut, capelin and herring, but not limited to these sources.

The process is preferably used on a commercial scale, that is, it is preferably applied to quantities of oil in excess of 1,000 kg.

The rendered, crude oil is preferably first treated with a silica gel under vacuum at a temperature high enough to reduce the oil's viscosity (preferably at the relatively low temperature of around 75° C.) and then with bleaching clay at temperatures which also reduce the oil's viscosity (preferably around 100° C.). After contact with these materials, they are separated from the oil by filtration or other means. The adsorbent-free oil is then preferably deodorized.

Further, it was found that such oils can be deodorized in modem, conventional edible oil deodorizing equipment to an odor-and flavorless oil under conditions which avoid isomerization of the very sensitive, long-chain, highly unsaturated fatty acids present. The process still removes pesticides to below detectable levels with low concentrations of free fatty acids and oxidation products. The resulting oils are especially suited for nutraceutical uses and in foods requiring oils of bland taste.

The need for soapstock byproduct and waste water processing was entirely avoided and oil losses in processing were significantly reduced.

The invention relates to a process of refining marine oil including:
  contacting the oil with an effective amount of a silica under a vacuum;
  contacting the oil with an effective amount of a bleaching clay;
  separating the silica from the oil;
  separating the clay from the oil.

The process is usefully performed without the use of an exogenously added alkali or acid.

In another variation, the process of is consisting of (or consisting essentially of):
  contacting the oil with an effective amount of a silica under a vacuum;
  contacting the oil with an effective amount of a bleaching clay;
  separating the silica from the oil;
  separating the clay from the oil.

In the process, the oil is contacted with the silica before the oil is contacted with the bleaching clay. In a process, the bleaching clay is under a vacuum.

The silica preferably includes a silica gel. The oil can be obtained from the fatty tissue of the marine mammal. The marine mammal may be a seal, for example, a harp seal, harbour seal, ringed seal, hooded seal and grey seal.

Oil from the fatty tissue of a fish can be used in the processes. The fish may be selected from the group including salmon and mackerel.

The silica and clay can be separated from the oil by filtration and/or centrifugation. The effective amount of silica gel is preferably from about 0.01% to 3% by weight of oil. The silica gel preferably includes TriSyl® S 627 silica gel or a Sorbsil® silica gel.

In the process, the oil is preferably contacted with the silica for about 1 to 60 minutes. The effective amount of bleaching clay is preferably from about 0.1% to 3% by weight of oil. The clay can include Tonsil Supreme 120 FF bleaching clay, a Filtrol bleaching clay or a Pur-Flog bleaching clay. The oil is preferably heated to about 75° C. to 110° C. after the oil contacts the bleaching clay. The oil preferably contacts the bleaching clay for about 5 to 30 minutes.

The process optionally further includes deodorizing the oil. The process of claim 20, wherein deodorization is carried out in the temperature range of about 150° C. to 245° C. Deodorization is preferably carried out at a pressure of about 0.1 mm Hg to 7 mm Hg. The oil is preferably exposed to the temperature and pressure for from about 0.5 minutes to 10 minutes. The oil shrinkage is preferably less than about 1.5%+1.5×FFA % in the oil by weight of crude oil. The refined oil is essentially free of proteinaceous material, phosphatidic material and mucilagenous material, trace metals and very low in colour. The refined oil preferably includes a free fatty acid content below 0.25% if the oil is deodorized and a free fatty acid content below 2% if the oil is not deodorized, a peroxide value less than about 1.5 me/kg, an anisidine value below 5 and iron below 0.1 mg/kg and a bland flavor. The refined oil preferably includes copper below about 0.05 mg/kg, phosphorous below about 0.2 mg/kg and is essentially free of pesticides. The omega-3 fatty acid concentration is preferably substantially unchanged from the crude oil. The omega-3 fatty acid concentration is preferably changed by less than 1% absolute from the crude oil. The oil preferably has a flavor stability measured by organoleptic testing in which no strong flavor development occurs for at least about 2 months when the oil is stored at ambient temperatures and substantially protected from harmful light radiation and air.

The invention also includes a refined marine mammal oil or seal oil prepared by a process of the invention. The invention includes a refined oil including a free fatty acid content below about 0.25% after deodorization and a free fatty acid content below 2% if the oil is not deodorized. The invention also includes a refined oil including a peroxide value less than about 1.6 mg/kg or a refined oil including an anisidine value below about 5. The refined is preferably a seal oil and includes a free fatty acid content below 0.25% after deodorization and and a free fatty acid content below 2% if the oil is not deodorized, a peroxide value less than about 1.5 me/kg, an anisidine value below 5, iron concentration below 0.1 mg/kg and a bland flavor. The oil preferably includes copper below about 0.05 mg/kg, phosphorous below about 0.2 mg/kg, and pesticides essentially undetectable by chromatography. The refined oil preferably has an omega-3 fatty acid concentration substantially unchanged from the crude oil. The refined oil preferably has a flavor stability measured by organoleptic testing in which no strong flavor development occurs for at least about 2 months when the oil is stored at ambient temperatures and protected from harmful light radiation and air. The oil includes marine mammal oil, for example, seal oil, such as harp seal, harbour seal, hooded seal, grey seal and ringed seal. The refined oil may also include fish oil. Blends of seal oils or fish oils may also be used. The fish oil can be selected from the group including salmon and mackerel. Shark oils are also useful.

Another aspect of the invention relates to an omega-3 fatty acid concentrate, including omega-3 fatty acids of the refined oil, concentrated by up to about 80% or 90%. The invention also includes a process for preparing an omega-3 fatty acid concentrate, comprising concentrating the omega-3 fatty acids of the refined oil by up to about 80% or 90%. The invention includes omega-3 fatty acids isolated from the oil of the invention.

Another aspect of the invention relates to a pharmaceutical composition including the refined oil of the inveniton and a carrier. The pharmaceutical composition may optionally include and carriers and/or diluents for adapting it for oral, nasal, pulmonary, rectal, ocular, transdermal or parenteral administration. They may be in combination with one or more bioactive compound(s), for example, at least one of coenzyme Q10 and an antioxidant.

The invention includes a nutritional supplement including the oil of the invention or omega-3 fatty acids of the invention. A nutritional supplement may also include oil or the omega-3 fatty acids and coenzyme Q10 or an antioxidant.

Another embodiment of the invention is a capsule including the oil or the omega-3 fatty acids. The capsule can include a gelatin capsule. Microcapsules are also useful.

Another aspect of the invention is a food product including the oil of the invention. The food product may include a milk product, a salad dressing or a grain product. The milk product may include skim milk, whole milk, 1% milk, 2% milk, sour cream, coffee cream, whipping cream, powdered milk, yogurt and ice cream. The grain product can include bread or baked food.

The invention also includes an animal, bird or fish feed including the oil or the omega-3 fatty acids of the invention. The invention also includes a food product, including the flesh or egg of an animal, bird or fish wherein the animal is raised by feeding the animal the oil, the omega-3 fatty acids or the feed of the invention.

The invention also includes a method of medical treatment, therapy or prophylaxis of a disease, condition, disorder or abnormal physical state including administering an effective amount of the oil, pharmaceutical composition, nutritional supplement, capsule or food product of the invention to a mammal or animal.

The disease, disorder or abnormal physical state can include one or more characteristics selected from the group consisting of inadequate dietary omega-3 fatty acids, an imbalance of essential fatty acids, a deficiency of one or more essential fatty acids including EPA. DHA, DPA, 18:3 omega-3 fatty acid and 18:4 omega-3 fatty acid. The disease can include heart disease, diabetes, hypertriglyceridemia, hypertension, arthritis, psoriasis, stroke, inflammation, immune system disorders or nervous system disorders. The invention also includes a method of medical treatment or prophylaxis of risk factors for a cardiovascular disease, disorder or abnormal physical state, including administering an effective amount of the oil, pharmaceutical composition, nutritional supplement, capsule or food product of the invention to a mammal. A variation of the invention includes a method for promoting normal brain, immune system and heart development in a patient which comprises administering to a mammal an effective amount of the oil, pharmaceutical composition, nutritional supplement, capsule or food product of the invention to a mammal. The invention also includes a method of prophylaxis of a disease, disorder or abnormal physical state in a fetus, infant or child comprising administering an effective amount of the oil, pharmaceutical composition, nutritional supplement, capsule or food product of any of the invention to a mammalian mother. The administered oil preferably includes omega-3 fatty acids selected from the group consisting of EPA, DHA, DPA, 18:3 omega-3 long chain fatty acids and 18:4 omega-3 long chain fatty acids. The amount of oil administered is preferably adequate to provide about 1.8 to 2.5 g or more of omega-3 essential fatty acids per day (for a human). The amount of harp seal oil preferably contains omega-3 essential fatty acids in the range of about 20% to 24% by weight and the amount of oil administered is preferably up to about 10 g/day. The amount of harp seal oil preferably contains omega-3 essential fatty acids in the range of about 20% to 24% by weight and preferably the amount of oil administered is less than or greater than about 10 g/day. The includes a refined seal oil having about the properties of the seal oil of the invention in one or more of Table 1–6.

The process preferably uses crude oil or foundation oil. The invention includes the use of the oil or the omega-3 fatty acids of the invention for the preparation of a medicament for the treatment of a disease in a mammal. The invention also includes an oil or the omega-3 fatty acids of the invention for use as an active pharmaceutical substance.

DETAILED DESCRIPTION OF THE INVENTION

Crude oil refers to oil that has been rendered. Crude oil also includes oil that has been centrifuged, allowed to sit for a period of time or otherwise treated so that undesirable components of the oil (eg. proteinaceous matter) settle out from the oil and can be removed.

The processes of the invention are preferably applied to crude oil but they may also be applied to "foundation oil" which refers to crude oil that has undergone one or more partial refinement processes, for example, degumming, desliming and/or water washing (but not alkali or acid refining). In a variation of the invention, other partial refinement processes to remove undesirable oil components (such as proteinaceous materials, phosphatides, mucilage, pro-oxidant metals or colored compounds) may also be used.

The crude oil is preferably obtained from the careful rendering of tissue from marine sources, mammalian and fish. To avoid damage to the highly sensitive EPA, DPA and DHA components (from heat, oxidation and contaminants), the oil is preferably heated to 50° C.–85° C., more preferably to 60° C.–80° C. and preferably to 75° C. in a batch reactor under vacuum to exclude air.

The vacuum is then broken and nitrogen is bubbled through the oil and a silica, preferably a silica gel, is added. Silica gels that are available for use with oils are suitable. For example TriSyl® S 627 silica gel (W. R. Grace, of Baltimore, Md., USA) is a suitable and preferred material. Silica gels are used in amounts of 0.01% to 3%, but more preferably in amounts of 0.1% to 1% and most preferably at 0.5%. Other useful silicas include Sorbsil® silicas (Crosfield Company, Joliet, Ill., USA).

Vacuum is restored and the silica is preferably contacted with the oil for 5 to 60 minutes, and more preferably for 10 to 30 minutes and most preferably for 15 minutes under agitation designed to keep the silica particles in uniform suspension.

The vacuum is then again broken and replaced with a nitrogen atmosphere and 0.1% to 3%, more preferably 0.5% to 2.0% and most preferably 1.0% of a bleaching clay commonly used for processing of oils is added. Tonsil Supreme 120 FF bleaching clay, which is manufactured by Quimica Sumex S.A. de C.V. of Mexico City, Mexico is a preferred clay, but other clays from the same manufacturer and clays from other manufacturers that are used for the purpose of processing oils may be used. For example, Filtrol bleaching clays (Engelhard Corp., Beachwood, Ohio, USA) and Pur-Flo® bleaching clays (Oil-Dri Corporation of America, Chicago, Ill., USA) are useful.

Vacuum is restored and the oil/silica/bleaching clay mixture is preferably heated to 75° C.–110° C., more preferably to 90° C. to 105° C., and most preferably to 100° C., and the oil is maintained in this temperature range for 5 to 30 minutes, and most preferably for 15 minutes under agitation. Agitation keeps the silica and clay particles in uniform suspension.

After this period, the oil may be cooled to a desired temperature and filtered, or the oil may be filtered at the treatment temperature and then cooled to a desired temperature. The filtered oil is kept under vacuum or a nitrogen gas blanket. Other means of separating the silica and clay from the oil may be used.

The above procedure can be performed in the continuous mode as well as in the batch mode, as will be apparent to those skilled in the art.

The above treatment may be preceded by a degumming process, with or without chemicals, or an alkali refining process using a suitable base. In chemical pretreatments, the benefit of not using any chemicals in the processing of the oil is no longer present.

The processing is completed by subjecting the filtered oil to deodorization under conditions designed to achieve a bland flavor, free fatty acids below 0.08%, no detectable pesticide concentrations and no change in the concentration of the long-chain, highly unsaturated fatty acids present. These conditions are preferably as follows:

A temperature of 150° C. to 245° C., and more preferably 200° C. to 240° C. and most preferably 232° C.

A pressure of 0.5 to 7 mm Hg absolute, and most preferably 2 to 3 mm Hg absolute.

A time at the above temperatures and pressures of 0.5 to 10 minutes, and more preferably from 2 to 7 minutes and most preferably 5 minutes.

A suitable amount of stripping gas, perferably steam or nitrogen.

Commercial scale equipment is available to achieve these process conditions.

EXAMPLE 1

2,400 kg of rendered harp seal blubber oil were pumped into a jacketed, stainless steel reactor equipped with an agitator, a nitrogen addition port and a vacuum system.

The reactor was sealed and evacuated and the oil was then heated to 75° C. under agitation.

Vacuum on the reactor was then broken with nitrogen gas and 0.5% TriSyl® S 627 silica gel was added to the oil. The reactor was then sealed again and evacuated. Temperature was maintained for 15 minutes of contact time of the silica/oil mixture. Vacuum was then broken with nitrogen gas, the reactor was opened, and 1% Tonsil Supreme 120 FF bleaching earth was added to the silica/oil mixture. The reactor was closed again, evacuated and the silica/clay/oil mixture was heated to 100° C. and kept at that temperature for 15 minutes contact time.

The mixture was then cooled to ambient temperature and filtered through a conventional plate & frame filter. The filtered, cooled oil was collected in a nitrogen gas-blanketed, stainless steel storage tank to await deodorization.

The above procedure was repeated with a further 2,400 kg batch of oil.

No waste water stream was produced in processing the oil for deodorization.

The two 2,400 kg batches of oil were then deodorized in a thin-film, continuous deodorizer at 230° C. and 2–3 mm Hg absolute pressure for 5 minutes exclusive of heating and cooling time.

The analytical data of the two combined, approximately 2,400 kg batches of crude, rendered oil, of the silica/clay treated oil and the analytical and organoleptic data of the deodorized oil are given in Table 1.

TABLE 1

|  | Crude | Silica/Clay Treat. | Deodorized. |
|---|---|---|---|
| *FFA, % | 0.48 | 0.5 | 0.06 |
| *PV, me/kg | 4.1 | 0 | 0 |
| *AV | 7.9 | 6.4 | 3.8 |
| Color, R/Y | 4.5/30 | 0.2/8.5 | 0.3/5.7 |
| Flavor./Odour | strongly fishy | fishy | bland/no odor |
| EPA + DPA + DHA, % | 20.3 | 20.4 | 20.1 |
| EPA, % | 7.6 | 7.6 | 7.5 |
| DPA, % | 4.1 | 4.1 | 4.0 |
| DHA, % | 8.7 | 8.7 | 8.6 |
| Phosph., P, mg/kg | — | — | — |
| Copper, Cu, mg/kg | — | — | — |
| Iron, Fe, mg/kg | — | — | — |
| Pesticides, mg/kg | — | — | <detection limit |

*FFA = free fatty acids; PV = peroxide value; AV = anisidine value (no units). A bland flavour or taste means that the oil does not have a fishy flavor (also referred to as a "strong flavour" in this application). A strong fishy flavor is unpleasant to most persons.
Note: All analyses were performed using the relevant Official Methods and Recommended Practices of the American Oil Chemists' Society, Champaign, IL, USA. For pesticides, AOAC Method 970-52-S of the Association of Official Analytical Chemists was used.

Comments on Crude and Processed Oil Quality Data, Table 1.

Crude oil was of relatively good quality. FFA, PV, color, were all acceptably low for oil rendered from edible seal blubber tissue. The AV at 7.9 was relatively high indicating some deterioration of the oil during the rendering process or crude oil storage.

Silica/clay treated oil was of excellent quality in respect to color and PV and AV. These data indicate that the oil pretreatment with the types and amounts of adsorbents chosen was removing the oil impurities of concern very thoroughly.

Deodorized oil was of excellent quality in all respects. Most striking was the completely bland taste of the freshly deodorized oil, which is a prerequisite for maintaining a relatively low taste level, if not a totally bland taste of the oil packaged in capsules bottles or incorporated into food recipes. Color, FFA, PV and AV were all at levels expected of the best edible vegetable oil or animal fat qualities on the market. Pesticide concentrations were below detection limits for present analytical chemistry methods. The concentration of the long-chain, highly unsaturated fatty acid components of the oil (EPA/DPA/DHA) remained unchanged in the silica/clay as well as in the deodorization treatment.

The above data show that degumming or alkali refining steps in processing of the seal blubber oil were not required to obtain a deodorized oil of excellent quality. It also shows that no chemicals such as acids or bases were required to achieve these results and that deodorization conditions chosen did not have any negative effects on oil quality.

EXAMPLE 2

The above described procedure was repeated with a slightly different lot of rendered, crude seal blubber oil. A total of about 15,000 kg of oil were silica/clay treated in seven approximately 2,200 kg batches. The analytical data of the seven combined batches of crude, rendered oil, of the combined silica/clay treated oil and the analytical and organoleptic data of the deodorized oil are given in Table 2.

TABLE 2

|  | Crude | Silica/Clay Treat. | Deodorized |
|---|---|---|---|
| *FFA, % | 0.49 | 0.5 | 0.07 |
| *PV, me/kg | 4.1 | 0.5 | 0 |
| *AV | 9.1 | — | 3.8 |
| Color, R/Y | 4.9/32 | 0.3/8.0 | 0.3/6.5 |
| Flavor./Odour | strongly fishy | fishy | bland/no odor |
| EPA + DPA + DHA, % | 20.4 | — | 20.3 |
| EPA, % | 7.6 | — | 7.5 |
| DPA, % | 4.1 | — | 4.1 |
| DHA, % | 8.7 | — | 8.7 |
| Phosph., P, mg/kg | 0.8 | <0.2 | <0.2 |
| Copper, Cu, mg/kg | <0.05 | <0.02 | <0.02 |
| Iron, Fe, mg/kg | 4.3 | <0.05 | <0.05 |
| Pesticides, mg/kg | — | — | <detection limit |

*FFA = free fatty acids; PV = peroxide value; AV = anisidine value (no units).
Note: All analyses were carried out using the Official Methods and Recommended Practices of the American Oil Chemists' Society, Champaign, IL, USA. For pesticides, AOAC Method 970-52-S of the Association of Official Analytical Chemists was used.

Comments on Crude and Processed Oil Quality Data, Table 2.

Crude oil was of relatively good quality. FFA and PV were acceptably low. The AV at 9.1 and the color at 4.9R/32Y were higher than in Example 1 indicating somewhat poorer crude oil quality than that used in Example 1. Iron concentration was 4.3 mg/kg, which is relatively high for satisfactory removal in refining procedures.

The silica/clay treated oil was of excellent quality in respect to color and PV and also in respect to AV (see deodorized oil data). The oil had low colour ("low colour" refers to below about 1 Lovibond red on a Lovibond colour comparator). Further, trace metals and phosphorus were essentially completely removed. These data indicate that the oil pretreatment with the types and amounts of adsorbents chosen was removing the oil impurities of concern very thoroughly. This is, of course, a prerequisite for producing a completely bland, odorless oil in deodorizing, as pointed out earlier. No byproducts requiring waste water treatment were produced.

Deodorized oil was of excellent quality in all respects. The oil was odorless and completely bland in taste. Color, FFA, and PV and AV, were all at levels expected of the best edible vegetable oil or animal fat qualities on the market. Iron, copper and pesticide concentrations were all below detection limits for present analytical chemistry methods.

There was no change in the concentration of the long-chain, highly unsaturated fatty acid components of the oil (EPA/DPA/DHA) as a result of deodorization under the conditions used.

During this relatively long production run, processing losses were determined to be about 2%. If alkali refining was used, a processing loss of 3.5% would be expected.

The above data confirm that degumming and alkali refining steps in processing of the seal oil were not required to obtain a deodorized oil of excellent quality by all criteria and that no chemicals were required to achieve this result.

We refine the procedure, for example, to increase silica gel quantity or to use a superior silica gel, and to use high quality seal oil (lower crude oil FFA, peroxide value, anisidine iron as well as other good quality indications) to obtain higher quality refined oil (peroxide value of zero, anisidine value below 2, and preferably below 1, iron below the detection limit, copper below the detection limit, phosphorous below 0.2 mg/kg, pesticides below their detection limits. We also use nitrogen stripping gas to get lower FFA.

We use the procedures described above, with necessary variations, to refine other crude marine oils (preferably seal and fish), including harbour seal, hooded seal, grey seal and ringed seal oils and salmon and mackerel oils (and other fish or seal oils). We measure the FFA, PV, AV, Color, R/Y, Flavour/Odour, EPA+DPA+DH (and individual percentages of these), phosphorous, copper and pesticides and determine that the refined oils have FFA<about 0.25% (when deodorized) and preferably <0.08, PV<about 1.5 and preferably about zero, AV<about 5 and preferably about 2, no flavour or odor (i.e. no fishy taste or odour-a bland oil), low colour, iron below about 0.1 mg/kg, copper below about 0.05 mg/kg, phosphorous below about 0.2 mg/kg, pesticides below their detection limits and a content of omega-3 fatty acids that is unchanged from the crude oil, within analysis error, and a flavor stability by organoleptic testing in which no strong flavor development occurs for at least 6 weeks at ambient temperatures when the sample is protected from harmful light radiation and from air, with or without the addition of antioxidants. We measure the stability of the oils after storage (preferably in capsules or brown glass bottles) at ambient temperatures (with or without tocopherols such as mixed tocopherols). The oils remain bland with no odour for at least 6 weeks.

Flavor Stability Evaluation of the Deodorized Oils

Samples of deodorized oil from the above examples were kept in brown glass bottles, nitrogen protected, and with and without 4,000 mg/kg of mixed, soybean oil-derived tocopherols added, at ambient temperature for up to 9 weeks. The samples were flavored by an expert in edible oil flavor evaluation. One sample was kept at 4.5 C without nitrogen protection.

Oil in capsules at ambient temperature was also evaluated. The results were as follows (tocoph. refers to tocopherol).

TABLE 3

|  | Oil from Example 1 | | Oil from Example 2 | |
| --- | --- | --- | --- | --- |
|  | with tocoph. | without tocoph. | with tocoph. | without tocoph. |
| Freshly deodorized | bland/no odor | | bland/no odor | |
| After 4 weeks | bland/ no odor | bland/ no odor | bland/ no odor | bland/ no odor |
| After 6 weeks | bland/ no odor | bland/ no odor | bland/ no odor | bland/ no odor |
| After 9 weeks | bland/ no odor | bland/ no odor | bland/ no odor | bland/ no odor |
| After 9 weeks, no nitrogen protect. at 4.5 C. | bland/ no odor | — | — | — |
| Oil in gelcapsules for 8 weeks | very slight fishy taste | — | — | — |

Comments on Flavor Stability Data, Table 3.

The above data show that the deodorized oil had excellent flavor stability in spite of its highly unsaturated components. The flavor data prove that the oil was essentially free of proteinaceous, mucilagenous and colored components, which might have led to flavor deterioration due to their breakdown over time and, which could occur independent of oxidation of the highly unsaturated components. The encapsulated oil is far superior in flavor to any capsule oil of marine origin presently available. Laboratory analysis was performed to compare the omega-3 seal oil capsules of the invention to commercially available seal oil capsules.

TABLE 4

QUALITY COMPARISON-LABORATORY ANALYSIS
OMEGA 3 SEAL OIL CAPSULES

| QUALITY INDICATORS | BRAND A | BRAND B | BRAND C | CAPSULES OF THE INVENTION |
| --- | --- | --- | --- | --- |
| ESSENTIAL FATTY ACID PROFILE | | | | |
| EPA mg | 27.93 | 32.75 | 32.43 | 39.05 |
| DPA mg | 15.19 | 18.40 | 18.88 | 21.01 |
| DHA mg | 35.28 | 37.31 | 37.27 | 43.52 |
| 18:3 OMEGA 3 mg | 2.45 | 2.35 | 2.42 | 2.91 |
| 18:4 OMEGA 3 mg | 6.37 | 5.57 | 6.29 | 6.81 |
| TOTAL OMEGA 3 mg/capsule | 87.22 | 96.38 | 97.29 | 113.30 |
| TOCOPHEROLS µg/capsule | 2205 alpha only | 390 | N/A | 2148 alpha, beta, gamma, delta |
| FREE FATTY ACIDS | 0.85% | 1.61% | 1.52% | 0.06% |
| PEROXIDE VALUE meq/kg | 11.7 | 4.85 | 1.57 | 0.40 |
| TBARS VALUE | 4.50 | 4.20 | 2.56 | 1.90 |
| TRACE Fe | TBD | TBD | TBD | NIL |
| METALS Cu | TBD | TBD | TBD | NIL |
| TOTAL PCB's/POLLUTANTS | 1.3 | 1.4 | 0.62 | NIL |
| COLOUR | YELLOW | YELLOW | YELLOW | LIGHT/ CLEAR |
| ODOUR | MILD FISHY | FISHY | FISHY | NO ODOUR |
| FLAVOUR | MILD FISHY WITH SLIGHT AFTER TASTE | FISHY WITH AFTER TASTE | MILD FISHY WITH AFTER TASTE | BLAND WITH NO AFTER TASTE |

*TBD = To be determined

Explanatory Notes on Table 4
1. All values are based on laboratory analysis of soft-gel, size 10 oval, nominal half-gram capsules sold commercially under the respective brand names.
2. Total omega-3 is a measure of the actual omega-3 content of oil as extracted from capsule samples and weighed. The omegas include EPA (eicosapentaenoic acid), DPA (docasapentaenoic acid), and DHA (docosahexaenoic acid) as well as the 18:3 omega3 and 18:4 omega3 fatty acids. The higher the omega3 content, the more valuable the oil. Note: Fish oils contain little or no DPA with mammalian oil constituting one of the few natural sources of this essential fatty acid.
3. The addition of mixed tocopherols serves as an antioxidant and helps preserve oil quality by absorbing the products of oxidation within the encapsulated oil. This also serves to extend the shelf life of the oil. Tocopherol levels for each brand are reported on the basis of the weight in micrograms per capsule. The capsules of the invention preferably utilize mixed tocopherols from natural sources.
4. Free fatty acids are produced during rendering of the oil and, if not removed during the refining process, can adversely affect colour, foam and cloudiness of the finished product.
5. The peroxide value is the measure of the primary products of natural oxidation in the oil. Reduction of the peroxides during refining to levels at or near zero is highly desirable in order to achieve an oil which is low in oxidation, high in oxidative stability and having maximum shelf life. Oil having peroxide values in excess of 3.0 meq/kg may be considered unacceptable in quality. Failure to reduce peroxides to sufficiently low levels may challenge the antioxidant defence mechanisms of the body and result in the creation of secondary products of oxidation.
6. The TBARS value is a measure of the secondary products of oxidation within the oil. It measures volatile compounds including anisidines which result form the breakdown of peroxides in the oil. The lower the TBARS value, the higher the quality of the oil. An oil having a high TBARS value may challenge the antioxidant defence mechanisms of the body and may exhibit a more pronounced fishy odour and taste, which even in encapsulated form may impair digestibility.
7. The level of trace metals in oil extracted from capsules of the invention is below detection limits. The presence of iron, in particular, is deemed undesirable as it presents a source of ongoing oxidation of the oil. Confirmation of the level of trace metals in other products is expected to be above detection limits.
8. The levels of pesticides, PCBs and other toxic materials in harp seal population in the North Atlantic is among the lowest among any marine mammals in the world and is well below all established international limits of toxicity. Nevertheless, the unique refining process of the invention has ensured the elimination of these background toxicants or their reduction below their respective detection limits.

EXAMPLE 3

The procedure described in Example 1 was repeated with another lot of rendered, crude seal blubber oil which had somewhat different crude oil quality parameters from those given in Examples 1 and 2. A total of about 20,000 kg of oil were silica/clay treated in nine approximately 2,200 kg batches. The analytical data of the nine combined batches of crude rendered oil, of the combined nine batches of silica/ clay treated oil and the analytical and organoleptic data of the deodorized oil are given in Table 4.

TABLE 4

| Analyses | Crude | Pretreated | Deodorized |
| --- | --- | --- | --- |
| *FFA, % | 0.53 | 0.54 | 0.03 |
| *PV, me/kg | 1.83 | 0 | 0 |
| *AV | 5.03 | 3.78 | 2.33 |
| Totox (2xPV + AV) | 8.7 | 3.6 | 2.3 |
| Color, R/Y | 5/26 | 0.5/11 | 0.3/9.9 |
| Flavor/Odor | strongly fishy | fishy | bland/no odor |
| EPA/DPA/DHA, % | 19.6 | — | 19.4 |
| EPA, % | 7.3 | — | 7.3 |
| DPA, % | 4.0 | — | 3.9 |
| DHA, % | 8.3 | — | 8.2 |
| Phosph., P, mg/kg | 0.8 | <0.2 | <0.2 |
| Copper, Cu, mg/kg | <0.05 | <0.05 | <0.05 |
| Iron, Fe, mg/kg | 0.53 | <0.02 | <0.02 |
| Pesticides, mg/kg | — | — | <det. limit |

*FFA = free fatty acids, PV = peroxide value, AV = anisidine value (no units).
Note: All analyses were carried out using the Official Methods and Recommended Practices of the American Oil Chemists' Society, Champaign. IL, USA, except the determination of pesticides which used Method 970-52-S of the Association of Official Analytical Chemists of the USA.

Comments on Crude and Processed Oil Data, Table 4.

Crude oil PV, AV and iron (Fe) content was lower than with the oil used in Examples 1 and 2 and FFA was about the same. The long-chain omega-3 fatty acids at 19.6% were lower than in the crude oil of Examples 1 and 2 at 20.4%. There was about 1.0% moisture in the crude oil (not listed in the table), which affected process losses.

The silica/clay treated oil was of excellent quality in respect to color, PV and AV.

Also, phosphorus, iron and copper were very low with iron and copper below the detection limits of accepted analysis methods. These results demonstrated again that alkali refining of the oil is not a prerequisite for preparing the oil for deodorization.

Deodorized oil was of excellent quality in all respects. The oil was odourless and essentially bland in taste. Colour, FFA, PV and AV were all at levels expected of the best edible oils of vegetable or animal origin on the market. Iron, copper and pesticides were below the detection limit. There was no significant change in the concentration of the long-chain omega-3 fatty acids EPA, DPA and DHA (19.4% vs. 19.6%) as a result of the deodorizing conditions used.

The processing losses in this run were determined to be about 3.7% of which about 2.6% were due to the silica/clay treatment and deodorization, and about 1.1% were due to moisture in the crude oil. If alkali refining had been used the losses would have been expected to about 1.5%, absolute, higher.

EXAMPLE 4

The procedure described in Example 1 was repeated with a fourth lot of rendered, crude seal blubber oil which had crude oil quality parameters similar to the oil used in Example 1, especially in respect to the peroxide value and the anisidine value of the oil. A total of about 20,000 kg of oil were silica/clay treated in nine approximately 2,200 kg batches, but only about 11,000 kg were deodorized because of deodorizer equipment problems. The analytical data of the nine combined batches of crude rendered oil, of the nine combined batches of silica/clay treated oil and the analytical and organoleptic data of the deodorized oil are given in Table 5.

The silica/clay treatment was chosen to be the same, initially, as used in the other examples, but this was changed after the first 2,200 kg batch from 0.5% TriSyl® 627 silica gel to 0.75%, and from 1% Tonsil Supreme 124 FF bleaching clay to 1.5% to try to improve pretreated oil colour, which was judged to be darker than desirable with the first batch processed.

TABLE 5

| Analyses | Crude (pre-ship sample) | Pretreated (batch spls averaged) | Deodorized (spot samples averaged) |
| --- | --- | --- | --- |
| FFA, % | 0.70 | 0.71 | 0.04 |
| PV, me/kg | 5.3 | 0.06–0.12 | 0–0.12 |
| AV | 6.5 | 4.5–5.4 | 2.1–3.0 |
| Totox (2xPV + AV) | 21.5 | 4.6–5.6 | 2.3–3.2 |
| Color, R/Y | 5.7/38 | 0.5/11 | 0.5/8 |
| Flav/Odor | strongly fishy | fishy | bland/no odor |
| *EPA/DPA/DHA, % | 19.7 | — | 19.5 |
| EPA, % | 7.2 | — | 7.1 |
| DPA, % | 4.0 | — | 4.0 |
| DHA, % | 8.5 | — | 8.4 |
| Phosph., P, mg/kg | <0.2 | — | <0.2 |
| Copper, Cu, mg/kg | <0.05 | — | <0.05 |
| Iron, Fe, mg/kg | 0.49 | — | <0.02 |
| Pesticides, mg/kg | — | — | <det. limit |

*FFA = free fatty acids, PV = peroxide value, AV = anisidine value (no units).
Note: All analyses were carried out using the Official Methods and Recommended Practices of the American Oil Chemists' Society, Champaign, IL, USA, except the determination of pesticides which used Method 970-52-S of the Association of Official Analytical Chemists of the USA.

Comments on Crude and Processed Oil Data, Table 5.

Crude oil quality was very similar to that of Examples 1 and 2 in respect to PV, AV and iron (Fe) content (Example 2, only). The FFA content was higher at 0.70% than in any of the previous examples, which had concentrations of about 0.50%. The long-chain omega-3 fatty acids at 19.7% were the same as in Example 3 (19.6%), but lower than in Examples 1 and 2 at 20.4%.

The silica/clay treated oil was of good quality, except that the colour of the first batch was 0.7 R, which was higher than experienced in the previous examples. With all subsequent pretreatment batches (8 out of a total of 9) Trisyl® silica gel was increased from 0.5% to 0.75% and Tonsil bleaching clay from 1% to 1.5%. This reduced colour by 0.2 R/5 Y to 0.5 R/8 Y similar to previous results. PV's and AV's were satisfactory.

Deodorized oil was of very good quality in all respects even though the PV measurements showed values in the range of 0.06–0.12 me/kg. The AV was very low, similar to the oil in Example 3. Phosphorus was at the desired low level and copper and iron were below their respective detection limits. Pesticides could not be detected in the oil. The long-chain omega-3 fatty acids remained essentially unchanged during deodorization (19.5% compared to 19.7% in the crude oil).

The processing losses in this run were determined to be about 4.5%. This was as expected from the higher FFA content and the higher usage of silica and clay.

Flavour Stability Evaluation of the Deodorized Oil Described in Table 5.

Samples of the deodorized oil from Example 4 containing 3,360 me/kg of mixed tocopherols derived from soybean oil were evaluated for flavour stability at 4–5 C (refrigerator temperature) in 150 ml food-approved, opaque plastic bottles. The bottles were nitrogen capped and wrapped in foil to ensure protection of the oil from light. One bottle/month, starting two days after the oil was deodorized, was flavour tested on every second or third day throughout the month by an expert taster by pouring a few ml of oil into a teaspoon and tasting it. After the tasting, the bottle was re-closed, without nitrogen cap, and returned to the refrigerator. After each month another bottle, which had been stored as above, was opened and tested as described above The results were noted by describing the flavour in terms commonly used in the edible oil industry from completely bland (and rarely achieved even with freshly deodorized animal fats or vegetable oils) to denoting a strongly fishy or painty taste and definitely no longer acceptable for consumption.

The results are summarized below in Table 6.

TABLE 6

| | Taste | |
| --- | --- | --- |
| Month | At start of month | At end of month |
| Month 1 | very slightly buttery, no fish note, nearly bland | slight fish taste, still quite acceptable |
| Month 2 | nearly bland, possibly a hint of fish | slight fish taste, slight oxidized note, still quite acceptable |
| Month 3 | nearly bland, very slight fish note, | slight fish and oxidized taste, still quite acceptable |
| Month 4 | nearly bland, very slight fish note | slight fish and oxidized taste, still quite acceptable |
| Month 5 | slight fish note, slightly bitter, | slight fishy/painty/oxidized taste still acceptable |
| Month 6 | nearly bland slight hint of fish | slight fish and slight bitter taste, still quite acceptable. |

Comments on Flavour Stability.

The above experience shows:

i) Oil in unopened bottles

The deodorized oil in bottles at 4–5 C under nitrogen gas and protected from light retained a nearly bland flavour for at least 6 months and very probably can be stored under these conditions much longer. There were some bottle-to-bottle differences due to handling of the samples and the sensitivity of omega-3 fatty acid oil to oxidation.

i) Oil in frequently opened bottles after 1 month

The deodorized oil after opening (and no longer under a nitrogen gas cap) deteriorates slowly over one month at 4–5 C. This deterioration still leaves the oil with an acceptable taste for use as a food after one month.

The flavour stability tests show that the oil was well refined, that is, it was essentially free of proteinaceous, mucilagenous and coloured components, which might have led to flavour deterioration due to the breakdown of these compounds over time and which would occur independently of oxidation of the highly unsaturated fatty acid components of the oil. Further, the tests indicate, that the oil is well-suited for the incorporation into many taste-sensitive foods that are normally being kept refrigerated.

Use of Refined Oil

The invention includes refined marine mammal oil or fish oil obtained according to the procedure outlined in the application. The oil is useful in the pharmaceutical, health food, supplement and food industries. The invention includes the use of an oil of the invention for the preparation of a medicament for the treatment of a disease in a mammal.

The invention also includes an oil of the invention for use as an active pharmaceutical substance.

The oil may be further processed after refining. For example, concentrate of omega-3 fatty acids could be prepared by known techniques to concentrate the omega-3 fatty acid content up to about 80% or 90%. One or more omega-3 fatty acids may also be separated from the oil. The separated fatty acids may then be used as nutritional supplements, neutraceuticals or pharmaceutical compositions in a similar manner as the whole refined oil.

Pharmaceutical, Nutritional Supplement Uses (i) Formulation

The refined oil may be administered to a mammal without formulation. Pharmaceutical compositions using the oil could include the oil and an acceptable vehicle or excipient (Remington's Pharmaceutical Sciences 18$^{th}$ ed, (1990, Mack Publishing Company) and subsequent editions). Vehicles include saline and D5W (5% dextrose and water). Excipients include additives such as an antioxidant (such as a mixed tocopherol, which includes alpha,- beta-, delta- and gamma-tocopherol), buffer, solubilizer, suspending agent, emulsifying agent, viscosity controlling agent, flavor, lactose filler, antioxidant, preservative or dye. The oil may be formulated in solid or semisolid form, for example pills, tablets, creams, ointments, powders, emulsions, gelatin capsules, capsules or gels. Capsules are the preferred dosage form. The capsules may include gelatin, glycerin, purified water and/or mixed tocopherol. Routes of administration include oral, topical, or transdermal administration optionally in combination with one or more bioactive compound(s). Preferred bioactive molecules are at least one of coenzyme Q10 and an antioxidant (e.g. mixed tocopherol). These formulations may also be used as a nutritional supplement or neutracetucal. The methods for the preparation of pharmaceutically acceptable compositions which can be administered to patients are known in the art.

The pharmaceutical compositions can be administered to humans or animals. Dosages to be administered depend on individual patient condition, indication of the drug, physical and chemical stability of the composition, toxicity, the desired effect and on the chosen route of administration (Robert Rakel, ed., Conn's Current Therapy (1995, W.B. Saunders Company, USA)). The pharmaceutical compositions are used as described in the following section.

The refined oil is useful to prevent, provide therapy for, or treat diseases, disorders, conditions and abnormal physical states where other omega-3 fatty acids and oils have proven useful. The oil is also a useful nutritional supplement for healthy individuals.

Some conditions typical of a deficiency in essential fatty acids are fatigue, depression, dry skin and hair, dry mucous membranes, cracked nails, indigestion, constipation and lack of endurance. The oil of the invention is useful to treat these conditions, whether or not they are caused by fatty acid deficiency.

Long term essential fatty acid deficiency is associated with a higher risk of chronic degenerative diseases. At least 60 medical conditions are linked to this deficiency or alternatively have been identified as benefiting from Omega-3 supplementation (Murray N D). Therapy, treatment or nutritional supplementation by administration of the oil (or omega-3 fatty acids separated from the oil) may be used to prevent or treat each of the diseases, disorders, conditions or abnormal physical states described in this application. The appropriate approach will be apparent based on the description in this application and the skill in the art. The diseases, disorders, conditions or abnormal physical states include hyperaggregation, cardiovascular disease and disorders (including hypercholesterolemia, atherosclerosis (Kanayasu-Toyoda T et al.; Dyerberg J) high triglyceride levels, impaired ability to circulate blood to the extremeties with the consequent atrophy of nerve cells-a particular problem for diabetics, and high blood pressure), atopic dermatitis, multiple sclerosis and premenstrual syndrome, acne, allergic and inflammatory conditions (including psoriasis and eczema (such as atopic dermatitis (endogenous eczema), seborrheic dermatitis and photodermatitis)), asthma (including difficulty breathing/shortness of breath, wheezing, coughing, production of bronchial mucus), autoimmune diseases (including multiple sclerosis (e.g. prevented in part by oil promotion of normal myelin formation)), lupus and some cancers), Alzheimer's disease, arthritis (particularly rheumatoid arthritis and osteoarthritis), atherosclerosis, breast cysts, cancer (including breast cancer), cystic fibrosis, diabetes, hypertension, hyperactivity, intestinal disorders kidney disfunction, leukemia, myopathy, obesity, homocystinuria and vascular disease. There is empirical evidence from health practitioners that seal oil has achieved remarkable results in a relatively short time frame among diabetics, persons with inadequate endocrine functions or enzyme functions, arthritic, psoriasitic and hypertensive patients. Administration of omega-3 fatty acids can change the chemical composition of organs (Murphy M G et al).

(ii) Diabetes

Diabetes is a disease which strongly benefits from administration of the oil of the invention. It is among the fastest growing medical conditions worldwide. Among the best known benefits of omega-3 seal oil is it ability to help restore blood circulation to the extremities (poor circulation can be a chronic problem among diabetics). Without proper circulation, nerve cells can atrophy and in the most severe cases result in blindness and the amputation of limbs. Omega-3 seal oil, preferably in conjunction with other dietary measures and exercise can help prevent or delay the onset of the disease.

(iii) Children

Omega-3 deficiency, particularly DPA & DHA deficiency can also contribute to problems in fetal development, vision (e.g. visual acuity), coronary hear disease and mental development in infants and children (Crawford Mass. et al.). Omega-3 fatty acids are critical to support proper child development and growth (for example, DHA is rapidly incorporated into the lipids of the brain and retina during the last trimester of pregnancy and the first year after birth.). They also protect against diseases such as those described above, and in particular hypertension, inflammation, allergies (Yu G, Bjorksten B; Yu G, Bjorksten B) autoimmune diseases, weakened immune system, liver degeneration, kidney degerneration, growth retardation, learning disorders, hypertension, eczema (Businco L et al.) and cardiovascular disease. Recent research has identified docosapentaenoic acid (DPA), for which EPA is a precursor, as among the most important of the EFAs in maintaining the required supple and pliable characteristics of interior vascular walls.

Infants, particularly premature infants, low birth weight infants, or infants for whom human breast milk is not available, benefit from infant formulas that include the oil of the invention. Malnourished children also benefit (Leichsenring M et al.). The formulas preferably use the oils to produce a milk with fatty acid composition similar to breast milk (preferably with additional omega-3 fatty acids; Henderson R A et al.). The formulas may be made rich in omega-3 fatty acids DHA, for example, to develop the nervous system and visual acuity.

Food Uses

The refined oil (or omega-3 fatty acids separated from the oil) is useful as a food additive, in order to fortify the nutritional content of food. Preferred foods include those with a short shelf life, such as a milk product or a grain product. Suitable milk products include skim milk, whole milk, 1% milk, 2% milk, sour cream, coffee cream, whipping cream, powdered milk, yogurt and ice cream. Milk prepared with the refined oil does not have a fishy taste and the oil does not add any odour. Preferred grain products include bread and flour. Bread prepared with the refined oil of the invention does not have a fishy taste and the oil does not add any odour. Foods with a longer shelf life such as salad dressing can also be fortified by the oil. Fruit and vegetable juices, such as orange juice, may also be fortified with the oil.

The refined oil is also suitable for addition to an animal, bird or fish feed. The invention includes a food product, comprising the flesh or egg of an animal, bird or fish where the animal is raised by feeding the animal the refined oil.

The oil may be microencapsulated according to known techniques for use in foods, pharmaceutical compositions or personal care products.

Formulation of a Personal-Care Product With Oil

Compositions for hair or other personal care may be prepared by adding oil in hair rinses, aerosol sprays, mists, gels, mousses, shampoos, conditioners, lotions, films, emulsions or colouring products.

The composition may be used in topical creams, such as moisturizers, makeup. Makeup products such as foundation, lipstick, eyeshadow, blush, moisturizing creams and lotions may also contain the oil of the invention. These are formulated according to known methods for makeup products such as those for preparation of an anhydrous or aqueous solid or paste, emulsion, suspension or dispersion.

The present invention has been described in detail and with particular reference to the preferred embodiments; however, it will be understood by one having ordinary skill in the art that changes can be made without departing from the spirit and scope thereof.

All publications, patents and patent applications, including Canadian application no. 2,260,397, are incorporated by reference in their entirety to the same extent as if each individual publication, patent or patent application was specifically and individually indicated to be incorporated by reference in its entirety.

REFERENCES

1. Benistant C, Achard F, Ben Slama S, Lagarde M, Docosapentaenoic acid (22:5,n-3): metabolism and effect on prostacyclin production in endothelial cells. *Prostaglandins Leukot Essent Fatty Acids* 1996 October;55(4): 287–92.
2. Shukla V K S and Perkins E G, The presence of oxidative polymeric materials in encapsulated fish oils. *Lipids* 26, 23–26, 1991.
3. Fritshe K L and Johnston P V, Rapid autoxidation of fish oil in diets without added antioxidants. *J. Nutr* 1118, 425–426, 1988.
4. Harats D, et al., Fish oil ingestion in smokers and nonsmokers enhances peroxidation of plasma lipoproteins. *Atherosclerosis* 90, 127–139, 1991.
5. Kromann N and Green A., Epidemiological studies in the Upernavik district, Greenland. *Acta Med Scand* 208, 401–406, 1980.
6. Kromhout D, Bosscheiter E B, and Delzenne-Coulander C, Inverse relation between fish oil consumption and 20 year mortality from coronary heart disease. *N. Engl J Med* 312, 1205–1209, 1985.
7. Seidelin K N, Myrup B, and Fischer-Hansen B, N-3 fatty acids in adipose tissue and coronary artery disease are inversely correlated. *Am J Clin Nutr* 55, 1117–1119, 1992.
8. Ornish E, et al., Can lifestyle changes reverse coronary heart disease. *Lancet* 336, 129–133, 1990.
9. Belch J F, et al., Effects of altering dietary essential fatty acids on requirements for non-steroidal anti-inflammatory drugs in patients with rheumatoid arthritis: A double blind placebo controlled study. *Annals Rheum Dis* 47, 96–104, 1988.
10. Murray N D, "The Encyclopedia of Nutritional Supplements"
11. Kanayasu-Toyoda T et al., "Docosapentaenoic acid (22:5, n-3), an elongation metabolite of eicosapentaenoic acid (20:5, n-3), is a potent stimulator of endothelial cell migration on pretreatment in vitro.", *Prostaglandins Leukot Essent Fatty Acids* 1996 May; 54(5):319–25 Med Res 1989 April;48(2):47–54.
12. Dyerberg J, "Coronary heart disease in Greenland Inuit: a paradox. Implications for western diet patterns."
13. Murphy M G et al., "Diets enriched in menhaden fish oil, seal oil, or shark liver oil have distinct effects on the lipid and fatty-acid composition of guinea pig heart.", *Mol Cell Biochem* 1997 December;177(1–2):257–69.
14. Crawford Mass. et al., "Essential fatty acids and fetal brain growth.", *Lancet* 1976 Feb. 28;1(7957):452–3.
15. Yu G et al., "Polyunsaturated fatty acids in school children in relation to allergy and serum IgE levels.", *Pediatr Allergy Immunol* 1998 August;9(3):133–8.
16. Yu G et al., "Serum levels of phospholipid fatty acids in mothers and their babies in relation to allergic disease.", *Eur J Pediatr* 1998 April; 157(4):298–303.
17. Businco L et al., "Breast milk from mothers of children with newly developed atopic eczema has low levels of long chain polyunsaturated fatty acids.", *J Allergy Clin Immunol* 1993 June;91(6):1134–9.
18. Leichsenring M et al., "Polyunsaturated fatty acids in erythrocyte and plasma lipids of children with severe protein-energy malnutrition.", *Acta Paediatr* 1995 May; 84(5):516–20.
19. Henderson R A et al., "Effect of fish oil on the fatty acid composition of human milk and maternal and infant erythrocytes.", *Lipids* 1992 November;27(11):863–9.

The invention claimed is:

1. A process of refining marine oil including:
   contacting marine oil which comprises crude oil with an effective amount of a silica under a vacuum;
   contacting the oil with an effective amount of a bleaching clay;
   separating the silica from the oil; and
   separating the clay from the oil.

2. The process of claim 1 wherein the process is performed without the use of an exogenously added alkali or acid.

3. The process of claim 1, consisting of:
   contacting marine oil which comprises crude oil with an effective amount of a silica under a vacuum;
   contacting the oil with an effective amount of a bleaching clay;
   separating the silica from the oil; and
   separating the clay from the oil.

4. The process of claim 1, wherein the oil is contacted with silica before the oil is contacted with the bleaching clay.

5. The process of claim 1, wherein the bleaching clay is under a vacuum.

6. The process of claim 1, wherein the silica includes a silica gel.

7. The process of claim 1, wherein the oil is obtained from the fatty tissue of the marine mammal.

8. The process of claim 7, wherein the marine mammal is a seal.

9. The process of claim 8, wherein the seal is selected from the group consisting of harp seal, harbour seal, ringed seal, hooded seal and grey seal.

10. The process of claim 1, wherein the oil is obtained from the fatty tissue of a fish.

11. The process of claim 10, wherein the fish is selected from the group consisting of salmon and mackerel.

12. The process of claim 1, wherein the silica and clay are separated from the oil by filtration and/or centrifugation.

13. The process of claim 6, wherein the effective amount of silica gel is from about 0.01% to 3% by weight of oil.

14. The process of claim 1, wherein the oil is contacted with the silica for about 1 to 60 minutes.

15. The process of claim 1, wherein the effective amount of bleaching clay is from about 0.1% to 3% by weight of oil.

16. The process of claim 1, wherein the oil is heated to about 75° C. to 110° C. after the oil contacts the bleaching clay.

17. The process of claim 1, wherein the oil contacts the bleaching clay for about 5 to 30 minutes.

18. The process of claim 1, including deodorizing the oil.

19. The process of claim 18, wherein deodorization is carried out in the temperature range of about 150° C. to 245° C.

20. The process of claim 18, wherein deodorization is carried out at a pressure of about 0.1 mm Hg to 7 mm Hg.

21. The process of claim 20, wherein the oil is exposed to the temperature and pressure of from about 0.5 minutes to 10 minutes.

22. The process of claim 1, comprising contacting the oil with the silica at a first temperature suitable for the silica to remove oxidation products and phosphatides from the oil and contacting the oil with the bleaching clay at a second temperature suitable for the bleaching clay to remove colored material and proteinaceous material from the oil.

23. The process of claim 22, wherein the first temperature comprises a temperature between 50° C. to 85° C. and the second temperature comprises a temperature between about 75° C. to 110° C.

24. The process of claim 22, wherein the first temperature comprises a temperature between 60° C. and 80° C. and the second temperature comprises between 75° C. to 105° C.

* * * * *